(12) United States Patent
Kim (10) Patent No.: US 10,874,515 B2
(45) Date of Patent: Dec. 29, 2020

(54) MITRAL CERCLAGE ANNULOPLASTY METHOD

(71) Applicant: June-Hong Kim, Busan (KR)

(72) Inventor: June-Hong Kim, Busan (KR)

(73) Assignee: TAU-PNU MEDICAL CO., LTD., Busan (KR)

( * ) Notice: Subject to any disclaimer, the term of this patent is extended or adjusted under 35 U.S.C. 154(b) by 214 days.

(21) Appl. No.: 16/226,630

(22) Filed: Dec. 19, 2018

(65) Prior Publication Data
US 2019/0269503 A1  Sep. 5, 2019

Related U.S. Application Data (60) Continuation of application No. 13/252,217, filed on Oct. 4, 2011, now Pat. No. 10,195,032, which is a division of application No. 12/631,803, filed on Dec. 4, 2009, now Pat. No. 82,316,171.

(60) Provisional application No. 61/239,828, filed on Sep. 4, 2009.

(30) Foreign Application Priority Data

Aug. 28, 2009 (KR) .................. 10-2009-0080708

(51) Int. Cl.
*A61F 2/24* (2006.01)
*A61B 17/04* (2006.01)

(52) U.S. Cl.
CPC .............. *A61F 2/246* (2013.01); *A61B 17/04* (2013.01); *A61B 17/0469* (2013.01); *A61F 2/2451* (2013.01); *A61F 2/2463* (2013.01); *A61B 2017/0496* (2013.01); *A61F 2/2466* (2013.01); *A61F 2250/0012* (2013.01)

(58) Field of Classification Search
CPC ...... A61F 2/246; A61F 2/2451; A61F 2/2463; A61F 2/2466; A61F 2250/0012; A61B 17/04; A61B 17/0469; A61B 2017/0496
See application file for complete search history.

(56) References Cited

U.S. PATENT DOCUMENTS

| | | | |
|---|---|---|---|
| 2003/0130731 A1* | 7/2003 | Vidlund | A61F 2/2487 623/2.37 |
| 2005/0216039 A1* | 9/2005 | Lederman | A61B 17/0487 606/144 |
| 2006/0184242 A1* | 8/2006 | Lichtenstein | A61F 2/2451 623/2.37 |
| 2016/0242908 A1* | 8/2016 | Kim | A61F 2/2451 |

* cited by examiner

*Primary Examiner* — Ashley L Fishback (57) ABSTRACT

A mitral cerclage annuloplasty apparatus comprises a tissue protective device and a knot delivery device. The tissue protective device comprises a first protective tube and a second protective tube. The knot delivery device comprises a tube wherein a loose knot is looped around its distal end through a hole and wherein tight knot is formed when the distal end of the tube is cut open. Alternatively, the knot delivery device comprises an inner tube and outer tube. The inner tube is insertable and rotatable inside the outer tube. When the tubes are in a closed position by rotating either the outer tube or the inner tube, a hole is created near its distal end. When the tubes are in open position by rotating either the outer tube or the inner tube, the hole joins the opening of the outer tube and lengthens.

22 Claims, 6 Drawing Sheets

MITRAL CERCLAGE ANNULOPLASTY METHOD

CROSS-REFERENCE TO RELATED APPLICATIONS

This is a continuation application for U.S. Ser. No. 13/252,217, filed Oct. 4, 2011 which is a divisional application for U.S. Ser. No. 12/631,803, filed on Dec. 4, 2009, which claims the benefit of U.S. Provisional Application No. 61/239,828 filed on Sep. 4, 2009 and claims foreign priority benefit of Korean Patent Application No. 10-2009-0080708 filed on Aug. 28, 2009 which is incorporated herein in its entirety.

FIELD OF THE DISCLOSURE

The present disclosure relates to annuloplasty devices and techniques in which coronary sinus and tricuspid valve is protected from erosion using a tissue protective device while maintaining appropriate tension by using a knot delivery device.

BACKGROUND

Heart is the center of human circulatory system that pumps blood through our body. It is a muscle that pumps the blood only in one direction. In order for the heart to effectively keep this unidirectional flow of blood, it must have properly functional valves that prevents back flow through its system, or regurgitation. Heart is divided into four chambers, right and left atrium, and right and left ventricles. The four chambers are connected to aorta, inferior and superior vena cava, pulmonary artery, and pulmonary veins.

Mitral valve ("MV") separates left atrium from left ventricle while tricuspid valve (TV) separates right atrium from right ventricle. Aortic valve ("AV") is located between left ventricle and aorta while pulmonary valve ("PV") is located between right ventricle and pulmonary artery.

Generally, valves should open and close completely with every heart beat or contraction. Incomplete opening and closing of the valves causes improper flow of blood. Valvular diseases are divided into two categories, regurgitation and stenosis. Regurgitation is a failure of valve to close completely and stenosis is a failure of valve to open completely.

Mitral valve regurgitation ("MVR") is a common cardiac valve disorder that is caused by incomplete closure of MV. MV is located between left atrium and left ventricle. Over time, MVR burdens the heart and worsens its ability to pump blood properly. Such stress on the heart will ultimately lead to heart failure.

Traditional treatment of worsening MVR requires an open heart surgery with sternotomy or thoracotomy with cardiac arrest and cardiopulmonary bypass. Once the chest is open and access to heart is gained, MV is either repaired or replaced using an artificial valve.

Although very effective, this open-heart procedure is a high risk surgery accompanied by substantial morbidity and prolonged convalescence. Mortality due to surgery itself can be as high as 5%. As a result, the procedure often is not offered to patients who are insufficiently symptomatic to justify the surgical risk and morbidity, or to patients with substantial co-morbidity. It is reserved only for those with severe symptomatic MVR.

This high morbidity rate of an open heart surgery has motivated further research to develop a safer and less risky alternative to repair MVR. Much of the research involves use of cardiac catheterization.

Recently, this inventor presented a thesis regarding "mitral valve cerclage coronary sinus annuloplasty (MVA)" showing outstanding result of MVR treatment through applying circular pressure around the mitral annulus. This thesis has been filed through PCT as an international patent application and published with its publication number WO2008/060553, which is incorporated herein in its entirety.

Aforementioned thesis and published patent application disclosed the mitral cerclage coronary annuloplasty ("MVA") procedure. Briefly explained, a catheter is placed at coronary sinus after accessing the right atrium through the jugular vein, and then a cerclage suture is passed through the proximal septal vein.

This cerclage suture can easily pass through right ventricular outflow tract ("RVOT"), and this inventor defines this technique as "simple mitral cerclage annuloplasty." Then the cerclage suture can be easily pulled into the right atrium thus placing the cerclage suture circumferentially around the mitral annulus.

Once positioned, tension is applied to the cerclage suture and tighten the mitral valve. This brings together the two leaflets of MV, so that they are approximated and reduce the size of its incomplete closure. This theory can obtain very similar result that conventional surgeries can obtain by directly tightening the mitral annulus, and show immediate reduction of MVR.

However, there are several technical problems to be solved. First, there is needed to have a tension locking device to be able to apply proper tension to the cerclage suture and maintain the tension.

According to the aforementioned research result, approximately 400-1200 g tension is needed to have good treatment result. In addition, individualized tension must be applied constantly until the point where the mitral regurgitation is reduced, then, the suture needs to be fixed at that point, so that the same tension is maintained. Further, this tension must be sustained regardless of constant resistance from every beat of each heart contraction.

Since this tension is maintained with a very fine cerclage suture (i.e., 0.014 nylon cerclage used in the researches), it can cause damages on the neighboring cardiac tissues where the suture contacts and exerts pressure. Especially, since the cerclage wraps around tricuspid valve (TV), it could affect the function of TV and damage the valve itself and its appendages. This invention is intended to provide viable solutions to overcome these problems.

SUMMARY

The objective of this invention is to overcome the shortcomings of conventional MVA. In addition, this invention provides techniques and devices designed for MVA to deliver proper, safe, and effective tension on the cerclage suture.

The other objectives are to provide a protective device for tissues and prevent damage from direct tissue to cerclage suture contact. In addition, it provides a knot delivery device ("KDD") which allows easier way of controlling, adjusting, and fixing the tension of the cerclage suture, so that it can be customized for each individual patient. It further provides tension locking function in which the fixed cerclage suture is maintained without becoming loose.

This invention achieves the aforementioned objectives by using an apparatus described here. Generally, the apparatus comprises a tissue protective device and a knot delivery device.

The tissue protective device comprises a first protective tube and a second protective tube. The first tube and the second tube each have a proximal portion and a distal portion. The proximal portions of the two tubes are attached side-by-side longitudinally. The distal portions of the two tubes are separated thereafter.

In a first embodiment, KDD comprises a tube having a proximal end, a hole, and distal end, wherein a loose knot is looped around the distal end through the hole and wherein tight knot is formed when the distal end of the tube is cut open.

In a second embodiment, KDD comprises an inner tube and outer tube. The inner tube and the outer tube each have a proximal end and a distal end. The inner tube is insertable and rotatable inside the outer tube. The distal ends of each tubes has an opening. The opening of the inner tube is further divided into a small opening and a large opening.

When the tubes are in a closed position by rotating either the outer tube or the inner tube, a hole is created near the distal end. In addition, when the tubes are in open position by rotating either the outer tube or the inner tube, the hole joins the opening of the outer tube and lengthens.

BRIEF DESCRIPTION OF THE DRAWINGS

FIG. 4(a) shows KDD whose distal end has a hole in a closed position where a loose knot is looped around the distal end through the hole.

FIG. 4(b) shows the distal end of the tube is cut off in open position where tight knot is formed.

FIG. 5(a) shows a step of making a loose knot around the distal end of KDD through the hole using cerclage suture.

FIG. 5(b) shows a step of tension adjustment where the suture can be pulled or released until the mitral regurgitation stops.

FIG. 5(c) shows a step of cutting off (or opening) the hole, so that the loose knot is ready to form a tight knot.

FIG. 5(d) shows a step of tightening the knot while maintaining the right amount of tension on the cerclage suture.

FIG. 5(e) shows a step of cutting off the cerclage suture.

FIG. 5(f) shows the final step of cerclage procedure.

FIG. 6(a) shows KDD in closed position where a hole is created near the distal end of KDD by rotating either the outer tube or the inner tube, so that a loose knot is formed around the distal end of KDD through the hole using cerclage suture.

FIG. 6(b) shows KDD in open position where an opening is created near the distal end of KDD by rotating either the outer tube or the inner tube, so that a loose knot is ready to form a tight knot without cutting in a step shown in FIG. 5(c).

DETAILED DESCRIPTION

The detailed disclosure of mitral valve cerclage coronary sinus annuloplasty ("MVA") comprising of coronary sinus and tricuspid valve protective device ("CSTVPD"), and a knot delivery device ("KDD") will be discussed.

Figure 1:
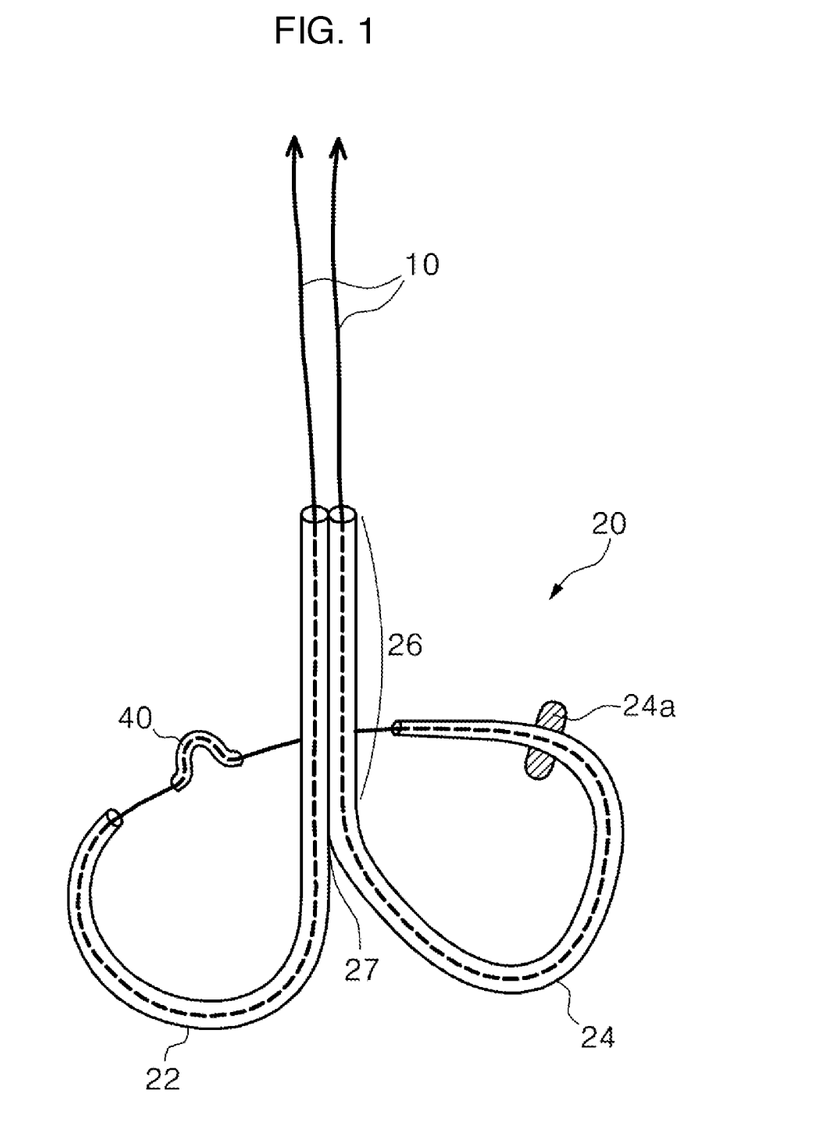
FIG. 1 shows a protection device in a particular embodiment, comprising a coronary sinus tube, a tricuspid valve tube, a hinge portion, a stem portion, a ring-shape stopper, a coronary protection device, and a cerclage suture.
Figure 2:
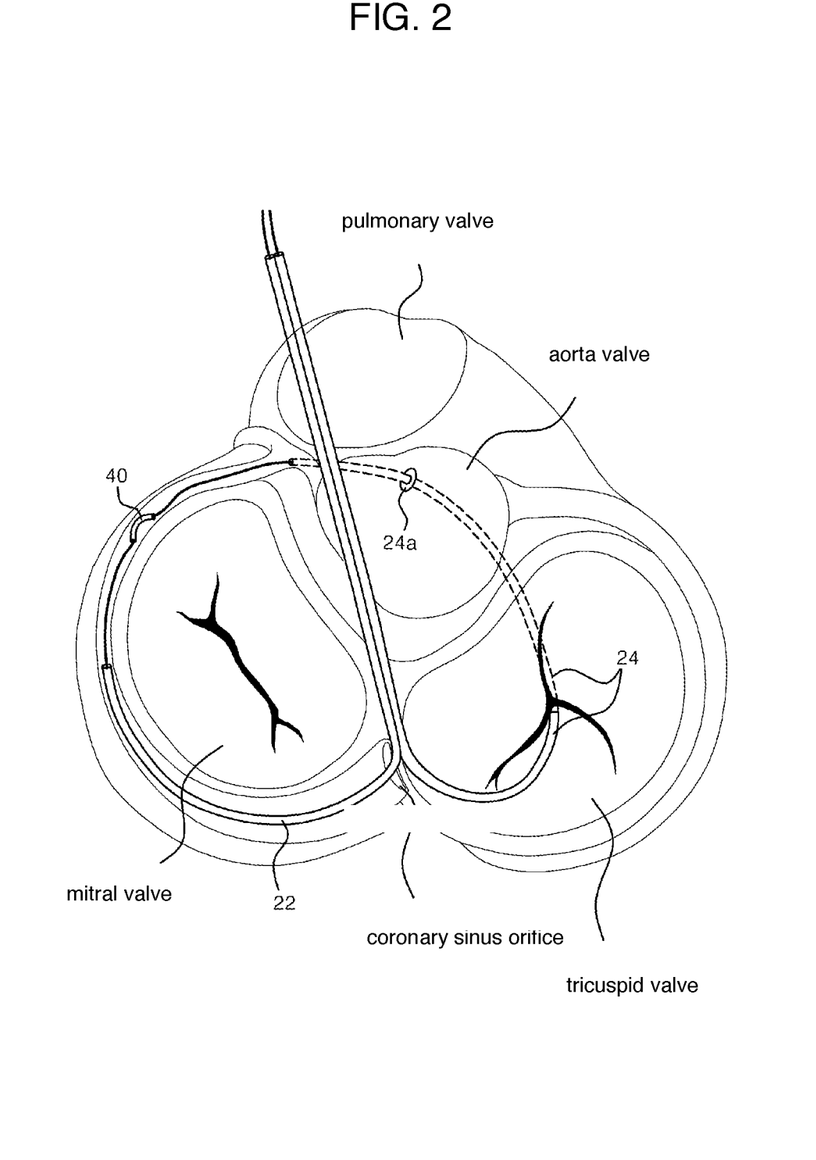
FIG. 2 is a schematic view of cross-sectional top of a human heart, taken at the level of the atrioventricular valves, showing the protective device in place.
Figure 3:
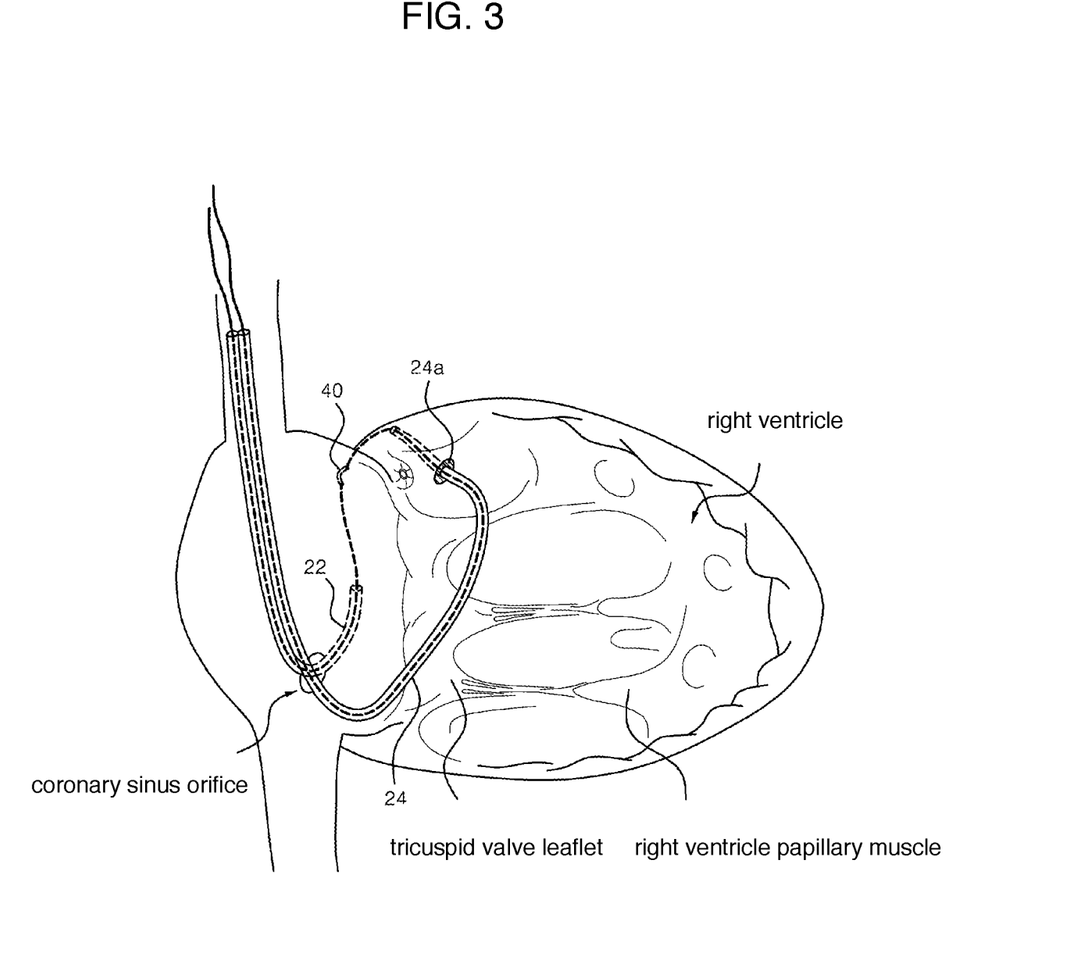
FIG. 3 is a front view of the heart with portions of the myocardial wall removed to show the protective device in place.

According to FIGS. 1-3, CSTVPD 20 comprises of a coronary sinus tube 22 ("CS tube"), a tricuspid valve tube 24 ("TV tube"), and stem portion 26. CS tube 22 encircles coronary sinus ("CS"), and TV tube 24 encircles tricuspid valve ("TV"). Then, extension of CS tube 22 and TV tube 24 meets and runs together to form stem portion 26.

Generally, conventional MVA techniques cause tissue damage (erosion) to CS, TV, and intraventricular septum ("IVS") from direct cerclage suture to tissue contact. These critical structures can be protected from damage by using CSTVPD 20 around the cerclage suture.

A part of CS is protected by coronary protective device 40 ("CPD") introduced in the previous MVA thesis. Thus, only the remainder of CS will need to be protected.

CSTVPD 20 has two separated tubes, CS tube 22 and TV tube 24 which extend and form stem portion 26. The thickness of the tubes are approximately 4 Fr diagnostic catheter made of flexible rubber or plastic like material. CSTVPD 20 is named because it protects both CS and TV.

In MVA procedure, first, a cerclage suture is fed through out CSTVPD 20 starting at CS extension of stem portion 26, CS tube 22, CPD 40, TV tube 24, and back out through TV extension of stem portion 26, or in reverse direction. Then, the suture-inserted CSTVPD 20 is pushed into the body through a catheter and positioned within the heart.

Then, CS tube 22 is positioned to wrap around cs, and tv tube 24 is positioned to traverse TV leaflets. Since the cerclage suture 10 is inside the tubes and not in direct contact with the surrounding tissue, cardiac tissues around cs, tv and IVS are protected from damage from the cerclage suture 10.

CS tube 22 is a part of a coronary sinus protection device. CS tube 22 starts at the orifice of CS to the beginning of CPD 40. Anatomically, this length varies from patient to patient. Thus, before the procedure, appropriate length can be determined using an estimation from CT or other imaging methods. CS tube 22 should be made of soft and flexible catheter like material, so that its affect on compression of CS is minimized.

TV tube 24 has tapering shape towards end. Starting from stopper 24a, TV tube 24 passes through the muscle of IVS. Therefore, in order to ease the passing through the IVS muscle, TV tube 24 should taper from stopper 24a to the end.

In addition, TV tube 24 has a ring-shaped stopper 24a (RVOT exit stopper 24a) positioned about mid length of TV tube 24 to prevent further advancement of TV tube 24 into the heart muscle.

Again, the length of TV tube 24 shall vary from patient to patient. The length shall be determined based on estimation from prior imaging studies of individual patient.

Preferably, the length of TV tube 24 from hinge portion 27 to stopper 24a shall be derived by actual endocardial surface length from 'RVOT exit' to 'CS opening.' It should be longer than actual endocardial surface length in order to be redundant. This distance from stopper 24a to the tapered end of TV tube 24 shall be determined by preintervention imaging analysis. Obviously, the location of stopper 24a can vary as needed, and the length from hinge portion 27 to stopper 24a can also vary depending on the need.

Hinge portion 27, where CS tube 22 and TV tube 24 meets, shall be placed at or near the orifice of CS. TV tube 24 will be fixed to the heart at hinge portion 27 and at stopper 24a. Then, hinge portion 27 to stopper 24a portion of TV tube 24 can be suspended freely in reverse "C" shape without being directly attached to the tissue. Such technique can reduce TV tissue damage resulting from direct contact of cerclage suture and it also reduces the restriction of cerclage on movement of TV leaflets.

TV tube 24 shall be rigid enough to resist being bent as tension is applied onto cerclage suture. On the other hand, it shall be flexible enough to bend in reverse "C" shape.

Stem portion 26 plays two roles. First, it stabilizes CS tube 22 and TV tube 24, so that their position is well maintained. Second, since hinge portion 27 rests on the orifice of CS, it prevents further advancement of CSTVPD 20 into the CS. Stem portion 26 (where CS tube 22 and TV tube 24 are adjoined) should be made of semi-rigid catheter like material.

Figure 4A:
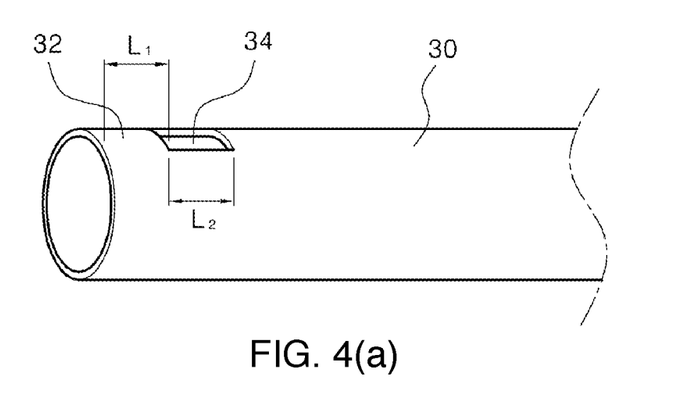
FIG. 4(a)-(b) is a set of drawings showing a knot delivery device ("KDD") in first embodiment using one tube configuration.
Figure 4B:
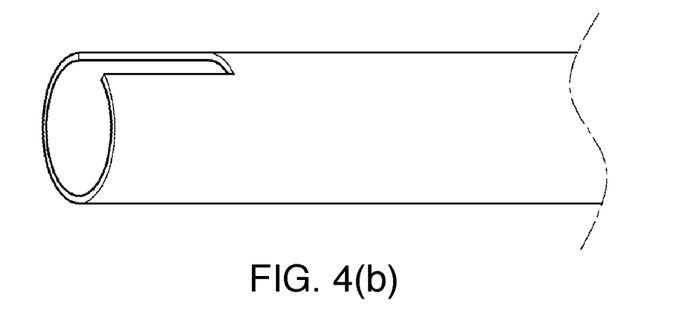

FIG. 4(a)-(b) shows a knot delivery device 30 ("KDD") in a first embodiment. KDD 30 is designed to transfer cerclage suture 10 looped and ready to be knotted to the upper portion of CSTVPD 20 while maintaining constant tension on the cerclage suture.

Once position and appropriate tension is verified, KDD 30 will release the loop and knot the suture in place thus ensuring the knot is positioned in the right place with appropriate amount of tension.

One of the most crucial component of MVA procedure is having a device that can deliver and maintain necessary tension enough to apply compression on mitral annulus. That device should be (1) easy to operate, (2) easy to manipulate cerclage suture tension depending on individual patient variance, (3) easy to readjust and fix tension (4) then once cerclage suture is fixed, not become loose and maintain constant tension well after the procedure.

FIG. 4(a)-(b) is a set of drawings showing KDD 30 in first embodiment using one tube configuration. FIG. 4(a) shows KDD 30 whose distal end has a hole in a closed position where a loose knot is looped around the distal end through the hole. FIG. 4(a) shows the distal end of the tube is cut off in open position where tight knot is formed. FIG. 4(b) shows the distal end of the tube is cut off in open position where tight knot is formed.

KDD 30 is a catheter where a portion 32 of the distal end of KDD 30 can be in closed position next to a hole 34 where a loose knot is looped around portion 32 through the hole. Portion 32 is cut off in opened position where the loose knot becomes a tight knot.

KDD 30 should be made of sturdy material often used in diagnostic catheters. It can be made of rubber or plastic like material strong enough to be pushed inside the body from outside.

As in FIG. 4(a) with portion 32 is in closed position, cerclage suture 10 is made into a loop ready to be knotted at the distal end of KDD 30. Then, KDD 30 with the loosely knotted cerclage suture 10 is advanced inside the body and positioned appropriately. Then tension is applied and adjusted. When position and tension is verified, portion 32 is cut off as in FIG. 4(b), fixing the knot in place while maintaining the same amount of tension on the cerclage suture.

FIG. 5(a)-(f) shows detailed steps of KDD 30 operation. FIG. 5(a)-(f) shows each steps of KDD 30 during MVA procedure.

Figure 5A:
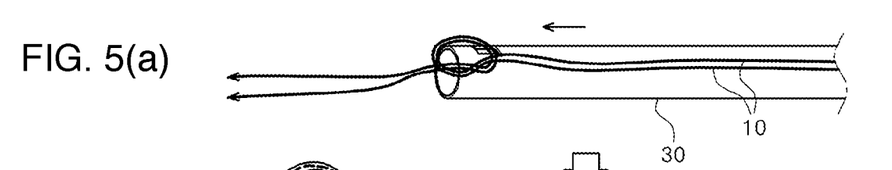
FIG. 5(a)-(f) is a set of drawings showing detailed steps of KDD operation in a first embodiment.
Figure 5B:
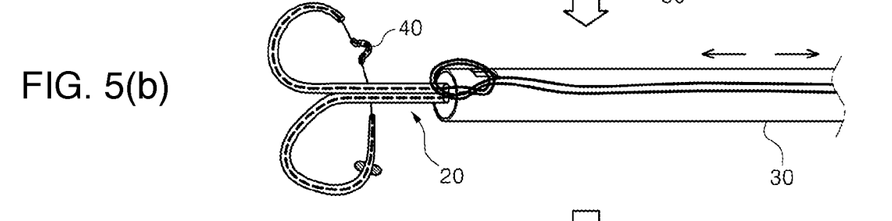

In summary, FIG. 5(a)-(f) is a set of drawings showing detailed steps of KDD 30 operation in a first embodiment. FIG. 5(a) shows a step of making a loose knot around the distal end of KDD 30 through hole 34 using cerclage suture 10. FIG. 5(b) shows a step of tension adjustment where suture 10 can be pulled or released until the mitral regurgitation stops.

Figure 5C:
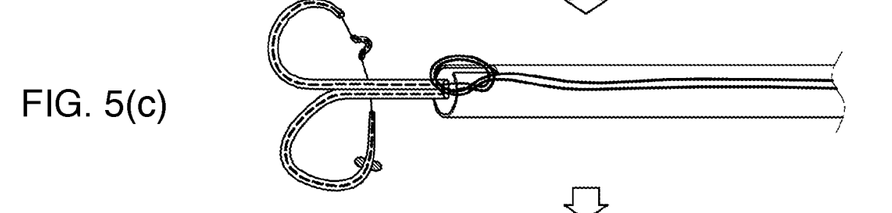
Figure 5D:
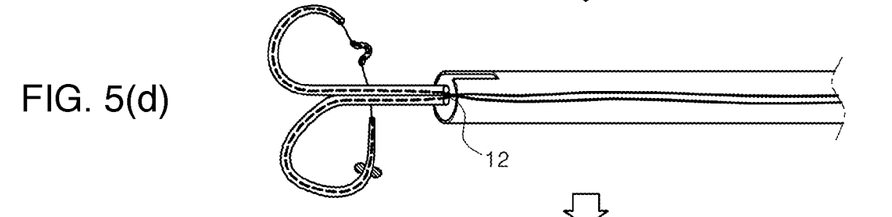
Figure 5E:
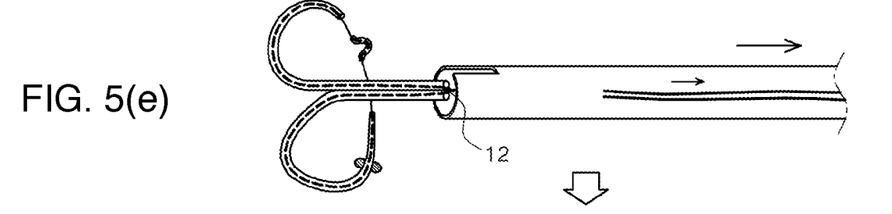
Figure 5F:
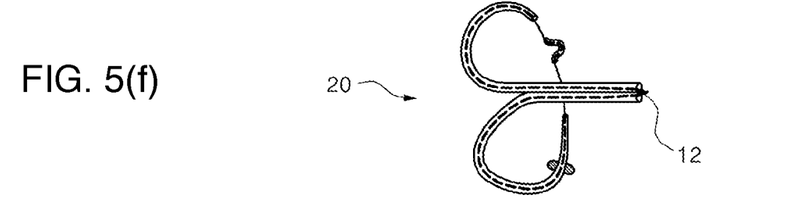

FIG. 5(c) shows a step of cutting off (or opening) hole 34, so that the loose knot is ready to form a tight knot 12. FIG. 5(d) shows a step of tightening the knot while maintaining the right amount of tension on the cerclage suture. FIG. 5(e) shows a step of cutting off the cerclage suture 10. Lastly, FIG. 5(f) shows the final step of cerclage procedure.

According to FIG. 5(a)-(f), first, two strands of the cerclage suture 10 are inserted through hole 34 at the distal end of KDD 30. Second, two strands are looped and made ready to form a knot 12. Third, the two strands are passed through the body of KDD 30. Fourth, KDD 30 is advanced into heart and positioned at the end of stem portion 26 of CSTVPD 20. Hence, KDD 30 delivers cerclage suture knot to CSTVPD 20 while keeping the knot 12 from tightening until it is ready to be fixed.

Then, appropriate amount of tension is applied to cerclage suture 10 and adjusted until mitral regurgitation ceases. In other words, tension on the cerclage suture 10 is adjusted by pulling or releasing the strands until the mitral regurgitation stops.

Once right amount of tension is achieved, portion 32 of KDD 30 is cut off from KDD 30. Portion 32 of KDD 30 can be cut with a cutter or as explained below in FIG. 4(a)-(b), various methods can be utilized.

When portion 32 is cut off from KDD 30, the loop tightens into a knot 12 while maintaining the right amount of tension on the cerclage suture as shown in FIG. 5(d), so that the end of cerclage suture is knotted at the distal end of stem portion 26 of CVTVPD 20. Once knot 12 is placed and tightened at the end of stem portion 26, stem portion 26 can now hold the two strands aligned and in place. This also enables knot 12 from becoming loose even under significant amount of tension from constant beat to beat contraction of the heart.

At this stage, the cerclage suture 10 is cut at a certain distance from the knot 12 with a cutter as shown in FIG. 5(e). And then, the remainder of the cerclage suture 10 and KDD 30 is retracted from the body as shown in FIG. 5(f). Thus upon completion of CSTVPD 20 procedure, CS tube 22 and TV tube 24 protects the surrounding tissue from cerclage suture 10 while maintaining constant tension on the cerclage suture 10.

Figure 6A:
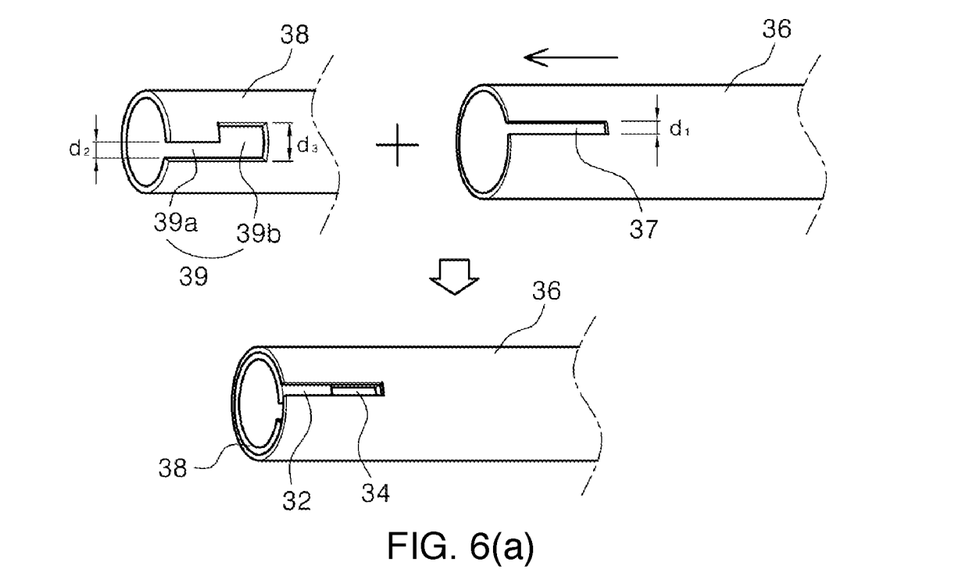
FIG. 6(a)-(b) is a set of drawings showing detailed operation of KDD in a second embodiment using an inner tube and an outer tube.
Figure 6B:
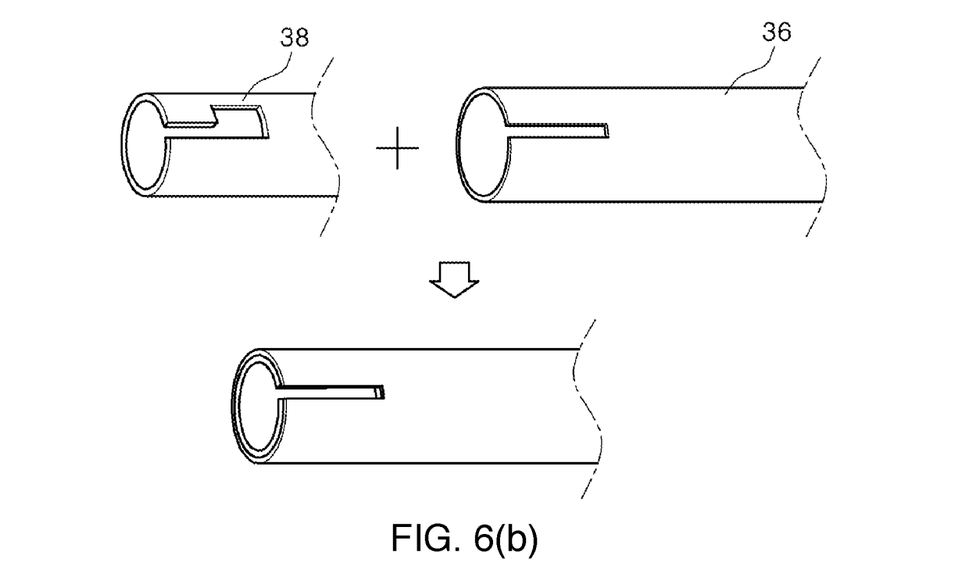

FIG. 6(a)-(b) is a set of drawings showing detailed operation of KDD 30 in a second embodiment using an inner tube 38 and an outer tube 36. Inner tube 38 and outer tube 36 each have a proximal end and a distal end. Inner tube 38 is insertable and rotatable inside outer tube 36.

The distal end of inner tube 38 has opening 39. The opening 39 is further divided into a small opening 39a and a larger opening 39b. The distal end of outer tube 36 has opening 37.

When the tubes 38, 36 in a closed position by rotating either outer tube 36 or inner tube 38, hole 34 is created near the distal end. Likewise, when the tubes 38, 36 in a opened position by rotating either outer tube 36 or inner tube 38, hole 34 joins opening 37 of outer tube 36 and lengthens. Outer tube 36 and inner tube 38 are made of basic catheter type of material.

FIG. 6(a) shows KDD 30 in closed position where hole 34 is created near the distal ends of KDD 30 by rotating either the outer tube 36 or the inner tube 38, so that a loose knot is formed around the distal ends of KDD 30 through hole 34 using cerclage suture 10.

FIG. 6(b) shows KDD 30 in open position where an opening is created near the distal ends of KDD 30 by rotating either the outer tube 36 or the inner tube 38, so that a loose knot is ready to form a tight knot 12 without a cutting step shown in FIG. 5(c).

In a preferred embodiment, inner tube 38 has the small opening whose length is L1 and diameter d2, and the large opening whose length is L2 and diameter d3, wherein outer tube 36 has length less than or equal to the sum of L1 and L2, and diameter d, and wherein d3 is wider or equal to the sum of d1 and d2.

While the invention has been described in terms of specific embodiments, it is apparent that other forms could be adopted by one skilled in the art. Accordingly, it should be understood that the invention is not limited to the specific embodiments illustrated in the Figures. It should also be understood that the phraseology and terminology employed above are for the purpose of disclosing the illustrated embodiments, and do not necessarily serve as limitations to the scope of the invention.

What I claim is:

1. A method of treating mitral valve regurgitation in a patient, comprising:
    positioning a cerclage suture to wrap around the mitral valve annulus;
    positioning a tube containing the cerclage suture to traverse a tricuspid valve;
    having loose ends of the cerclage suture meet in the right atrium; and
    pulling the loose ends of the cerclage suture to apply tension until mitral regurgitation is reduced.
2. The method of claim 1, wherein the tube containing the cerclage suture is pushed out through a catheter.
3. The method of claim 1, wherein the tube containing the cerclage suture takes a "C"-shape as it traverses a tricuspid valve leaflet.
4. The method of claim 3, wherein the "C"-shape portion of the tube is suspended freely without being directly attached to heart tissue.
5. The method of claim 1, wherein the cerclage suture is wrapped around the mitral valve annulus by passing the cerclage suture into the proximal septal vein.
6. The method of claim 1, further comprising feeding the cerclage suture into the tube prior to positioning to traverse the tricuspid valve leaflet.
7. The method of claim 1, wherein the tube has a stopper at a distal portion of the tube.
8. The method of claim 7, further comprising selecting the distance of the stopper from the distal end of the tube by preintervention imaging analysis.
9. The method of claim 1, further comprising embedding the distal end of the tube into heart muscle.
10. The method of claim 9, wherein the tube has a stopper at a distal portion of the tube and the stopper prevents further advancement of the tube into the heart muscle.
11. The method of claim 1, where the tube has a tapered shape at its the distal end.
12. The method of claim 1, where the tube is approximately 4 French size.
13. The method of claim 1, wherein the cerclage suture inside the tube does not make direct contact with the surrounding tissue.
14. The method of claim 1, further comprising selecting the length of the tube by reviewing prior imaging studies of the patient.
15. The method of claim 1, wherein the tube is a first tube and wherein the cerclage suture encircling the mitral valve annulus is contained in a second tube that is separate from the first tube.
16. The method of claim 15, wherein the proximal end of the first tube and the proximal end of the second tube meet at a hinge portion formed by the conjunction of the two tubes.
17. The method of claim 16, wherein the hinge portion of the two tubes is placed at or near the coronary sinus orifice of the heart and serves to prevent further advancement of the tubes into the coronary sinus orifice.
18. The method of claim 16, wherein the distance from the hinge portion to a stopper of the first tube is longer than actual endocardial surface length.
19. The method of claim 1, further comprising:
    inserting the proximal end of the cerclage suture into a knot delivery catheter;
    knotting the cerclage suture at the distal end of the knot delivery catheter;
    advancing the knot delivery catheter to advance the knot towards the tube; and
    tightening the cerclage suture knot.
20. The method of claim 19, wherein the step of knotting the cerclage suture comprises inserting the suture through a hole at the distal end of the knot delivery catheter.
21. The method of claim 19, further comprising cutting the cerclage suture at a position proximal to the knot.
22. The method of claim 1, wherein the cerclage suture is advanced into the coronary sinus, into the proximal septal vein, around the mitral valve annulus, around a tricuspid valve leaflet, through the heart muscle, and out into the right atrium.

* * * * *